United States Patent [19]

Tan

[11] Patent Number: 4,773,415
[45] Date of Patent: Sep. 27, 1988

[54] LENS POSTERIOR CAPSULE INSTRUMENT

[76] Inventor: Ben G. Tan, 20924 Kelly Rd., East Detroit, Mich. 48021

[21] Appl. No.: 810,782

[22] Filed: Dec. 19, 1985

Related U.S. Application Data

[63] Continuation-in-part of Ser. No. 703,753, Feb. 21, 1985, abandoned.

[51] Int. Cl.$^4$ .............................................. A61B 17/00
[52] U.S. Cl. ................................... 128/303 R; 128/20; 128/24 A
[58] Field of Search ............... 128/303 R, 304, 20, 128/24 A, 305; 433/136; 604/22, 1

[56] References Cited

U.S. PATENT DOCUMENTS

| | | | |
|---|---|---|---|
| 2,791,226 | 5/1957 | Kurz | 132/50 R |
| 3,618,594 | 11/1971 | Banko | 128/303 R |
| 3,896,552 | 7/1975 | Russell | 604/1 |
| 3,996,935 | 12/1976 | Banko | 604/22 |
| 4,283,809 | 8/1981 | Prost | 604/1 |

Primary Examiner—John Weiss
Attorney, Agent, or Firm—John R. Benefiel

[57] ABSTRACT

An instrument and technique is disclosed for protection of lens posterior capsule of the eye during cataract operation. The instrument consists of a length of fine surgical wire mounted at one end in a tubular handle with the tip angled and coated with silicone rubber. The instrument is used in conjunction with the phaco-emulsification removal technique using an ultrasonic instrument, by positioning the coated tip of the instrument intermediate the posterior capsule and the cataract lens nucleus. The cataract lens nucleus is held away from the posterior capsule by manipulation of the instrument during the phaco-emulsification procedure, with the tip protecting the posterior capsule from the action of the ultra-sonic instrument.

9 Claims, 2 Drawing Sheets

LENS POSTERIOR CAPSULE INSTRUMENT

CROSS REFERENCE TO RELATED APPLICATIONS

This application is a continuation-in-part of Ser. No. 703,753 filed on Feb. 21, 1985 abandon.

BACKGROUND DISCUSSION

The present invention pertains to an instrument for protecting the posterior capsule of the lens during cataract surgery by a small wound incision technique, commonly known as phaco-emulsification.

In recent years, two surgical techniques for removing a cataract from the eye are employed, the large wound incision technique, and the small would incision technique also referred to as phaco-emulsification. Intraocular lens implants are used with both techniques. In the large wound incision technique, a large incision almost half the circumference of the cornea is made, and the cataract is expressed or squeezed out of the eye manually. The main advantage of this technique over phaco-emulsification is that it is easier to perform. The disadvantages are that it takes a much longer time to recuperate due to the large wound, and also creates more astigmatism.

The small wound incision technique, illustrated in FIGS. 1 and 2, employs an ultra-sonic aspirating needle 10 which cuts the cataract 12 into tiny pieces and aspirates them out of the eye. This is accomplished through a small opening 14 on the eye wall. The advantages are that the eye recuperates faster, the patient returns to work sooner, and less astigmatism results. The disadvantages are that it is a more difficult technique, and requires expensive instruments.

The main cause of difficulty with this technique is the problem of breaking the lens posterior capsule 16. An intact, unbroken posterior capsule is important for the well-being of the eye after the operation. During surgery, only the substance of the cataract is removed, and the posterior capsule (the back cellophane-like envelope of the cataract lens) is left intact, and remains inside the eye. It is important to leave the posterior capsule intact for the success of the operation, since vitreous will be released through any break or tear and if this happens good vision may not be achieved, and serious complications will likely result later. An intact posterior capsule is essential for ideal placement of an intra-ocular lens implant.

Since the cataract nucleus and the posterior capsule are located very close to each other, the danger of breaking or damaging the posterior capsule by the powerful ultra-sonic tip is constantly present. A good analogy is the task of cutting a pie directly on top of a table cloth.

It is a difficult task fraught with tension and anxiety.

Accordingly, the object of the present invention is to provide an instrument that is used during surgery for removal of a cataract by phaco-emulsification which will effectively protect the posterior capsule from the powerful ultrasonic cutting tip.

SUMMARY OF THE INVENTION

This and other objects of the present invention, which will become apparent upon a reading of the following specification and claims, are achieved by the use of a special instrument consisting of a length of wire mounted within a handle with the tip of the wire being angled and coated with a soft, but durable, cushioning material such as silicone rubber. During use, the instrument tip is inserted into the space between the posterior capsule and the cataract lens nucleus, and manipulated to position the cataract lens nucleus to be spaced substantially away from the posterior capule to minimize the possibility of damage to the posterior capsule during use of the ultrasonic probe.

Preferably, the instrument is designed to be disposable and for this purpose the handle is formed of thin-walled, hollow plastic tube in which is anchored the angled wire as by means of a molded material retained within the end of the plastic tube.

In the preferred embodiment, the wire comprises a coated tip section joined to an extension section extending from the handle, with an intermediate section offsetting and angling the tip so as to allow positioning of the catract lens nucleus away from the posterior capsule, to minimize the possibility of injury to the posterior capsule during phaco-emulsificatary removal of the cataract nucleus.

The main feature of the instrument is the microscope-precision made tip which is composed of a fine diameter steel wire angulated at approximately 90 degrees horizontally from the main wire shaft. Half the length of this working tip is precisely coated with medical silicone which has a uniform external diameter of 0.025 inch. A short distance, away from the first angulation, there is another angulation of approximately 130 degrees and at the opposite direction from the first one. This second angulation makes it possible to comfortably hold the instrument handle at approximately 45 degrees orientation during the surgery. The main wire shaft is mounted on a light-weight plastic tube, $\frac{1}{4}$ inch in diameter which allows it to be held like a pencil. The fine profile of the instrument working tip allows it to be inserted inside the eye through a tiny stab incision on the wall of the eye. The tip, being coated with silicone rubber is smooth, soft, nontraumatic when it comes in contact with the delicate posterior capsule, yet it is tough, resistant, practically indestructible to the powerful ultra-sonic cutting tip. This feature makes it very useful during the cataract surgery. Thus, this instrument practically serves as a cutting board inside the eye, preventing the ultra-sonic cutting tip from cutting into the posterior capsule.

DETAILED DESCRIPTION

In the following detailed description, certain specific terminology will be utilized for the sake of clarity and a particular embodiment described in accordance with the requirements of 35 USC 112, but it is to be understood that the same is not intended to be limiting and should not be so construed inasmuch as the invention is capable of taking many forms and variations within the scope of the appended claims.

Figure 1:
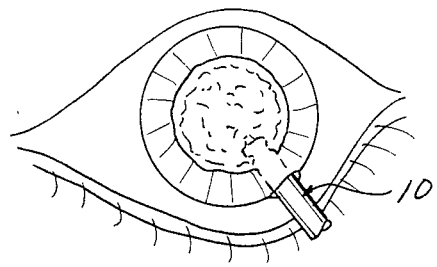
FIG. 1 is a frontal view of an eye on which a small wound or phaco-emulsification cataract removal surgery is being performed.
Figure 2:
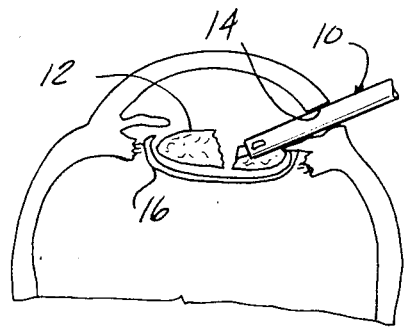
FIG. 2 is a sectional view of an eye on which a small wound or phaco-emulsification cataract removal surgery is being performed.
Figure 3:
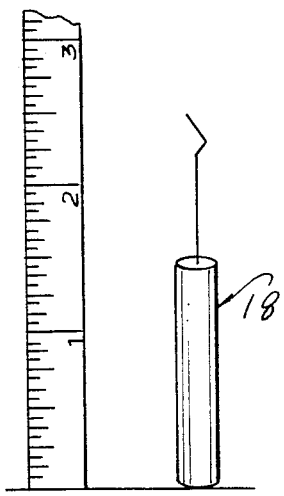
FIG. 3 is a full size perspective view of an instrument according to the present invention, with a reference scale.
Figure 4:
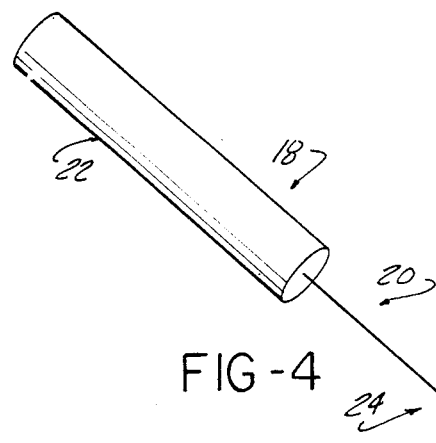
FIG. 4 is an enlarged perspective view of an instrument according to the present invention.
Figure 5:
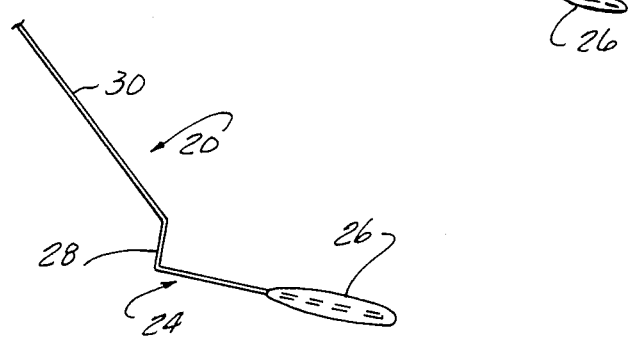
FIG. 5 is a greatly enlarged view of the tip of the instrument shown in FIG. 4.
Figure 6:
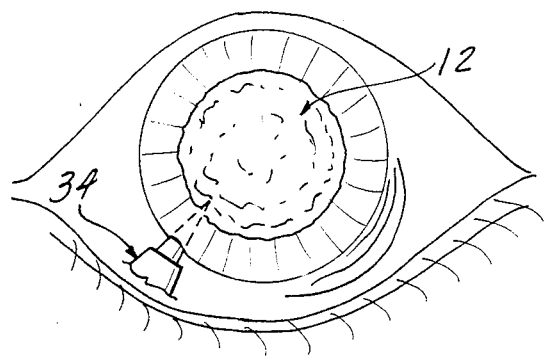
FIG. 6 is an inverted frontal view of an eye in which a separate stab incision is being made for the passage of the instrument into the eye.

Referring to the drawings and particularly FIGS. 3–5, the instrument 18 according to the present invention consists of a length of wire 20 mounted within an elongated, tubular handle 22, to extend therefrom in a generally parallel direction to the axis of the tubular handle 14.

The functioning part of the instrument 18 is the tip 24, which is approximately 5/16 of an inch (7 mm) long made of a fine diameter stiff steel wire 0.012 inch (±0.003") of suitable surgical material, such as stainless steel.

The distal half of the tip 24 is precision fusion coated with a mass of silicone rubber 26, with a uniform external diameter of approximately 0.025". The tip 24 is angulated at 90 degrees from an intermediate offsetting section 28 shaft, this angulation serving to limit the length of the instrument able to be inserted inside the eye during surgery to be described hereinafter to no more than the length of the tip 24, i.e., 5/16 inch. The intermediate section 28 is connected to an extension section 30 angulated at approximately 130 degrees (±5 degrees) thereto in the opposite direction. This second angulation enables the instrument handle 22 to be held comfortably in hand like a pencil at 45 degrees at the point of contact with the eye.

According to one aspect of the present invention, the instrument is contemplated as being packaged presterilized, and is disposable to eliminate any need for resterilization after use. For this purpose, a thin-walled, hollow plastic tube may be employed as the handle 22 having a mass of molded material 32, such as silicone rubber, filling either end of the plastic tube and serving to anchor the extension section 30 of the length of wire 20 therein.

The thin-walled plastic tube may be of a diameter of ¼ inch and of a length of 1½ inches to enable easy manipulation during use and of a sufficient size for secure handling during use.

Thus, a lightweight, low cost construction may be achieved suitable for disposable instruments.

Referring to FIGS. 6–10, a stab incision is first made with instrument 34 into cornea at the 2 o'clock position (eye shown inverted, for a surgeon's view), the working tip 24 of the instrument 18 is inserted into the eye at 2 o'clock stab incision. The ultra-sonic cutting tip 10, which has been inserted through a separate previously made incision at 11 o'clock, is withdrawn slightly.

Figure 7:
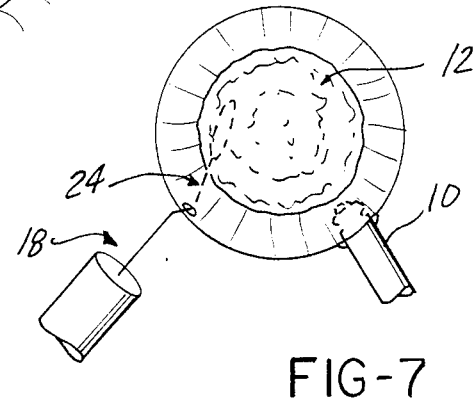
FIG. 7 is an inverted frontal view of the eye in which the instrument is inserted into the eye through the stab incision.
Figure 8:
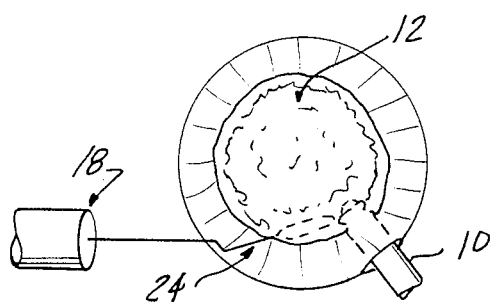
FIG. 8 is an inverted frontal view of the eye in which the instrument is being swept behind the cataract.

As shown in FIG. 7, the cataract nucleus 12 is gently depressed with the tip 24 of the instrument 18 which tilts the superior pose of the cataract nucleus 12 upward. The ultra-sonic instrument 10 is advanced into anterior chamber to hold the tilted cataract nucleus 12 at iris plane as shown in FIG. 8. While holding the tilted cataract nucleus 12 with the ultra-sonic tip 10 the instrument tip 24 is swept behind the cataract nucleus 12 and in front of the posterior capsule.

Figure 9:
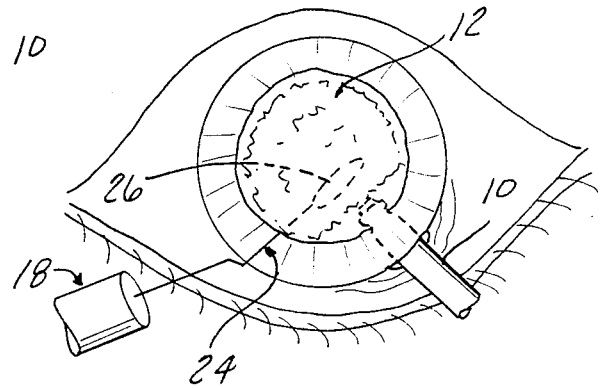
FIG. 9 is an inverted frontal view of the eye in which the instrument is placed behind the cataract but in front of the posterior capsule.
Figure 10:
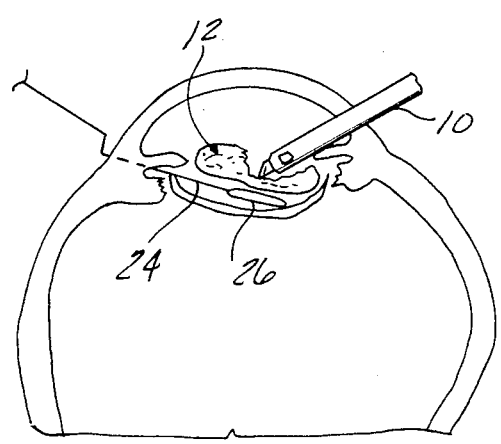
FIG. 10 is a sectional view of the eye in which the posterior capsule is now protected from the ultra-sonic cutting needle, with the instrument placed in front of the posterior capsule.

Now referring to FIG. 9 and 10, the posterior capsule 16 is now protected with the instrument tip 24 and cushioning mass 26 placed between the cataract nucleus 12 and the posterior capsule 16 and enabling the cataract nucleus 12 to be held away from posterior capsule 16.

Phaco-emulsification, i.e., removal of the cataract nucleus 12 by use of ultra-sonic cutting aspirating needle, may then proceed safely to completion.

It can be appreciated that this instrument can be manufactured at low cost and made to be used as a disposable instrument to eliminate the needs and risks of resterilization of the instruments after surgery prior to reuse.

I claim:

1. A surgical instrument for protecting the lens posterior capsule while performing cataract lens nucleus removal eye surgery comprising:
    an elongated handle;
    a length of fine diameter surgical wire mounted to and extending from said handle with a tip section comprised by the free end of said length of wire; and,
    a mass of soft durable smooth material molded to said tip section and coating at least a portion of said tip section to cushion and protect the posterior capsule during cataract surgery.

2. The instrument according to claim 1 wherein said length of wire includes an extension section extending from said handle, and generally parallel thereto, and also includes an intermediate offset section joining said tip and extension sections angled to laterally offset said tip section from said extension section.

3. The instrument according to claim 1 wherein said mass of soft durable material comprises silicone rubber coating said tip section of said instrument.

4. The instrument according to claim 1 wherein said handle is formed of a length of hollow tubular plastic and molded material is disposed in either end thereof, with said length of wire anchored in said molded material at one end of said plastic tube.

5. The instrument according to claim 3 wherein said cushioning mass coats the tip section to a diameter on the order of 0.025 inch.

6. The instrument according to claim 1 wherein said length of wire is of a diameter on the order of 0.012 inches in diameter.

7. The instrument according to claim 2 wherein said tip section is on the order of 5/16ths inch in length and angled at approximately 90 degrees to said intermediate section to limit the length of insertion of said tip section.

8. The instrument according to claim 7 wherein said intermediate section is angled approximately 130 degrees to said extension section.

9. An improved technique for performing cataract lens nucleus removal surgery by phaco-emulsification, including the steps of removing the cataract lens by means of manipulation of an ultrasonic probe into contact with the contact lens, the improvement comprising:
    the step of inserting into the intermediate space between the cataract lens nucleus and posterior capsule a wire tip coated with a mass of soft cushioning material and manipulating said tip so as to displace the cataract lens nucleus away from the posterior capsule during manipulation of the ultrasonic probe.

\* \* \* \* \*

UNITED STATES PATENT AND TRADEMARK OFFICE
CERTIFICATE OF CORRECTION

PATENT NO. : 4,773,415
DATED : September 27, 1988
INVENTOR(S) : Ben C. Tan

It is certified that error appears in the above-identified patent and that said Letters Patent is hereby corrected as shown below:

Column 1, line 16, "would" should be --wound--.

Column 2, line 6, "capule" should be --capsule--.

Column 2, line 18, "catract" should be --cataract--.

Signed and Sealed this

Twenty-eighth Day of February, 1989

Attest:

DONALD J. QUIGG

Attesting Officer      Commissioner of Patents and Trademarks